(12) United States Patent
Chen

(10) Patent No.: US 8,152,742 B2
(45) Date of Patent: Apr. 10, 2012

(54) CROSSING GUIDE WIRE WITH CORRUGATED SHAPING RIBBON

(75) Inventor: Hancun Chen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 773 days.

(21) Appl. No.: 11/414,993

(22) Filed: May 1, 2006

(65) Prior Publication Data

US 2007/0255183 A1    Nov. 1, 2007

(51) Int. Cl.
  *A61B 5/00* (2006.01)
  *A61M 25/00* (2006.01)
  *A61F 11/00* (2006.01)

(52) U.S. Cl. .................................. 600/585; 606/108

(58) Field of Classification Search ................... 600/585; 606/108

See application file for complete search history.

(56) References Cited

U.S. PATENT DOCUMENTS

| | | | |
|---|---|---|---|
| 4,554,929 A | 11/1985 | Samson et al. | |
| 4,827,941 A | 5/1989 | Taylor et al. | |
| 4,846,186 A | 7/1989 | Box et al. | |
| 5,007,434 A | 4/1991 | Doyle et al. | |
| 5,304,198 A * | 4/1994 | Samson | 606/194 |
| 5,313,967 A | 5/1994 | Lieber et al. | |
| 5,365,943 A | 11/1994 | Jansen | |
| 5,534,007 A * | 7/1996 | St. Germain et al. | 623/1.11 |
| 5,605,162 A * | 2/1997 | Mirzaee et al. | 600/585 |
| 5,609,130 A * | 3/1997 | Neumann | 123/267 |
| 5,673,707 A | 10/1997 | Chandrasekaran | |
| 5,762,615 A * | 6/1998 | Weier | 600/585 |
| 5,772,609 A | 6/1998 | Nguyen et al. | |
| 5,788,653 A * | 8/1998 | Lorenzo | 600/585 |
| 5,931,819 A | 8/1999 | Fariabi | |
| 6,004,279 A | 12/1999 | Crowley et al. | |
| 6,016,848 A * | 1/2000 | Egres, Jr. | 138/137 |
| 6,113,557 A * | 9/2000 | Fagan et al. | 600/585 |
| 6,123,712 A * | 9/2000 | Di Caprio et al. | 606/108 |
| 6,139,510 A | 10/2000 | Palermo | |
| 6,159,227 A * | 12/2000 | Di Caprio et al. | 606/192 |
| 6,183,420 B1 * | 2/2001 | Douk et al. | 600/462 |

(Continued)

FOREIGN PATENT DOCUMENTS

EP    0 823 261 A2    2/1998

(Continued)

OTHER PUBLICATIONS

International Search Report PCT/US2007/063881; report dated Aug. 23, 2007.

(Continued)

*Primary Examiner* — Max Hindenberg
*Assistant Examiner* — Sean Dougherty
(74) *Attorney, Agent, or Firm* — Seager, Tufte & Wickhem LLC

(57) ABSTRACT

A medical device with a corrugated shaping ribbon is provided. The corrugated shaping ribbon for the medical device, which may be provided in the form of a guide wire or catheter, specifically a crossing guide wire or catheter, provides a mechanism by which energy can be stored as the distal tip of the medical device engages a lesion or other area of occlusion within a blood vessel. By storing such energy and continuing to apply force, eventually the distal tip extends thereby releasing the stored energy and allowing the distal tip to advance or cross through the lesion.

10 Claims, 2 Drawing Sheets

U.S. PATENT DOCUMENTS

| | | | |
|---|---|---|---|
| 6,308,090 B1 * | 10/2001 | Tu et al. | 600/374 |
| 6,364,144 B1 * | 4/2002 | Jakob et al. | 220/4.02 |
| 6,419,685 B2 * | 7/2002 | Di Caprio et al. | 606/192 |
| 6,428,489 B1 | 8/2002 | Jacobsen et al. | |
| 6,464,651 B1 * | 10/2002 | Hiejima et al. | 600/585 |
| 6,638,266 B2 | 10/2003 | Wilson et al. | |
| 7,044,921 B2 * | 5/2006 | Asmus et al. | 600/585 |
| 7,077,811 B2 | 7/2006 | Vrba et al. | |
| 7,118,539 B2 * | 10/2006 | Vrba et al. | 600/585 |
| 7,141,024 B2 * | 11/2006 | Gaber | 600/585 |
| 2002/0072737 A1 * | 6/2002 | Belden et al. | 606/34 |
| 2002/0156519 A1 * | 10/2002 | Di Caprio et al. | 623/1.11 |
| 2003/0114911 A1 * | 6/2003 | Lupton | 623/1.11 |
| 2003/0163064 A1 * | 8/2003 | Vrba et al. | 600/585 |
| 2004/0049148 A1 * | 3/2004 | Rodriguez et al. | 604/22 |
| 2004/0111044 A1 * | 6/2004 | Davis et al. | 600/585 |
| 2004/0193139 A1 * | 9/2004 | Armstrong et al. | 604/523 |
| 2004/0254450 A1 | 12/2004 | Griffin et al. | |
| 2005/0096665 A1 | 5/2005 | Reynolds et al. | |
| 2005/0145307 A1 | 7/2005 | Shireman et al. | |
| 2006/0201604 A1 * | 9/2006 | Wilson et al. | 156/86 |
| 2007/0021775 A1 * | 1/2007 | Vrba et al. | 606/200 |
| 2009/0234279 A1 * | 9/2009 | Goldstein | 604/95.01 |

FOREIGN PATENT DOCUMENTS

| | | |
|---|---|---|
| EP | 1 287 846 A2 | 3/2003 |
| WO | WO 2004/012804 A2 | 2/2004 |

OTHER PUBLICATIONS

Written Opinion of International Application No. PCT/US2007/063881.

* cited by examiner

CROSSING GUIDE WIRE WITH CORRUGATED SHAPING RIBBON

FIELD OF THE DISCLOSURE

The field of the disclosure generally relates to medical devices and, more particularly, relates to medical devices for insertion into body lumens such as blood vessels or other vasculature.

BACKGROUND OF THE DISCLOSURE

In many modern medical procedures, it is common to introduce devices intravascularly so as to minimize the traumatic effect on the patient. For example, in an arteriotomy, wherein an occlusion or blockage of a blood vessel is widened or cleared so as to improve blood flow, it is common to navigate a balloon catheter to the site of the occlusion, inflate the balloon, and thus expand the diameter of the blood vessel in the location of the occlusion. Once expanded, it is often then common to insert a stent to the site of the occlusion so as to hold the blood vessel in an open position and thus prevent the blood vessel walls from contracting radially inwardly after withdrawal of the balloon.

In order to navigate the balloon catheter to the site of the occlusion, it is first necessary to navigate a guide wire to the location. As the balloon catheter itself is relatively soft and malleable, it can not be directed to the site of the occlusion through the blood vessel without a stiffening member along which it can ride. That stiffening member is typically provided in the form of the aforementioned guide wire. Guide wires themselves are relatively stiff or at least have relatively stiff shafts so as to be easily pushed through the blood vessel by the physician or other technician. However, in order to minimize the potential for damage to the blood vessel walls, the distal tip of the guide wire is provided in a relatively soft and malleable form. It is common for the tips of such guide wires to include a polymer sleeve which is soft enough to bend and contort as the guide wire navigates through the sometimes tortuous pathways of the blood vessel, but which also has sufficient strength as provided by the guide wire itself to allow it to be pushed, turned, and otherwise manipulated through the blood vessel. It is still further possible to use a shaping ribbon to provide the very distal tip of the guide wire with improved shape-ability.

While effective, it is still desired in the medical community to provide guide wires with even better performance characteristics. Those characteristics include shape-ability, track-ability and cross-ability. With respect to cross-ability, it is often necessary for the distal tip of the guide wire to cross through the lesion or other occlusion within the blood vessel. Such lesions and occlusions are often relatively hard substances which are difficult for the guide wire to advance through given the need for the guide wire itself to be relatively soft for the purpose of navigating the guide wire through the vasculature. One solution which has been tried has been to make the distal tip of the guide wire relatively hard, but the force with which the guide wire can be advanced is necessarily limited by the overall strength of the entire guide catheter and not just the tip. Accordingly, not only must the guide wire have good cross-ability, i.e., an ability to cross through a lesion or other occlusion, but good shape-ability as well meaning that it can deflect or otherwise deform as the guide wire is navigated through the vasculature.

A still further attribute which guide wires should have is good track-ability, meaning the ability to follow the sometimes tortuous pathways of human blood vessels. In other words, the better the ability of the guide wire to advance through the twists and turns of the blood vessel to get to the site of the occlusion, the better its track-ability.

SUMMARY OF THE DISCLOSURE

In accordance with one aspect of the disclosure, the crossing guide wire is disclosed which comprises a core wire having a proximal end and a distal end, a corrugated shaping ribbon extending from the distal end of the core wire, and a sleeve positioned over the corrugated shaping ribbon and at least a portion of the core wire.

In accordance with another aspect of the disclosure, a method of directing a guide wire to a desired location with a body lumen is disclosed which comprises introducing the guide wire into a body lumen, the guide wire having a core wire, a corrugated shaping ribbon extending from the core wire, and a sleeve over the corrugated shaping ribbon and at least a portion of the core wire, the guide wire terminating in a distal tip, the corrugated shaping ribbon being deformable between compressed and un-compressed states; pushing the guide wire through the body lumen until the distal tip engages a site of occlusion in the body lumen, the corrugated shaping ribbon being deformed into the compressed state as the guide wire is further pushed; and continuing to push the guide wire until the corrugated shaping ribbon extends through the site of occlusion, the corrugated shaping ribbon returning to its uncompressed state after extending through the site of occlusion.

In accordance with another aspect of the disclosure, a crossing guide wire is disclosed which comprises a core wire having a proximal end and a distal end, a spring extending from the core wire distal end, and a sleeve positioned over the spring and at least a portion of the core wire.

In accordance with another aspect of the disclosure, a medical device is disclosed which comprises a core wire having a proximal end and distal end, the distal end being adapted to navigate through a body lumen, and a spring extending from the core wire distal end.

These and other aspects and features of the disclosure will become more readily apparent upon reading the following detailed description when taken in conjunction with the accompanying drawings.

Figure 1:
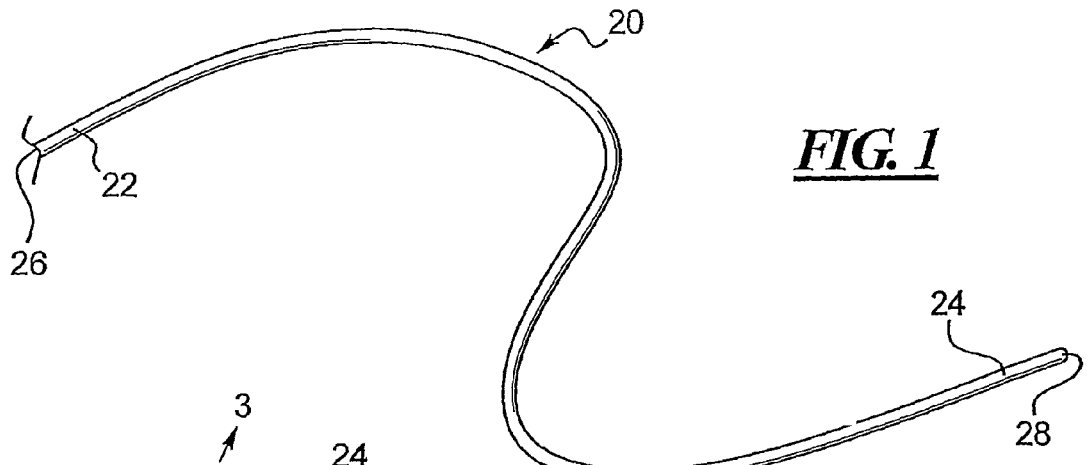
FIG. 1 is a plan view of a illustrative elongate medical device constructed in accordance with the teachings of the disclosure, and shown as a guide wire.
Figure 2:
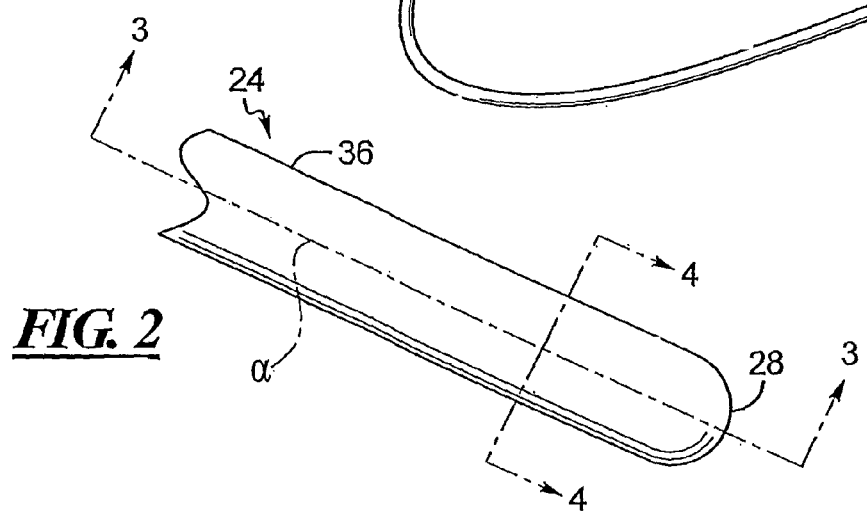
FIG. 2 is an enlarged perspective view of the distal tip of the guide wire of FIG. 1.

While the present disclosure is susceptible to various modifications and alternative constructions, certain illustrative embodiments thereof have been shown in the drawings and will be described below in detail. It should be understood, however, that there is no intention to limit the disclosure to the specific forms disclosed herein, but on the contrary, the intention is to cover all modifications, alternative constructions, and equivalents falling within the spirit and scope of the disclosure as defined by the appended claims.

DETAILED DESCRIPTION OF THE DISCLOSURE

Referring now to the drawings and with specific reference to FIG. 1, a plan view of a medical device constructed in accordance with the teachings of the disclosure is generally referred to by reference numeral 20. In addition, while the depicted medical device is shown in the form of a guide wire, it is to be understood that the teachings of the disclosure can be used in constructing any number of different medical devices, specifically elongated medical devices for intravascular introduction including, but not limited to, guide catheters, guide wires, balloon catheters, probes, scopes, and the like.

Figure 5:
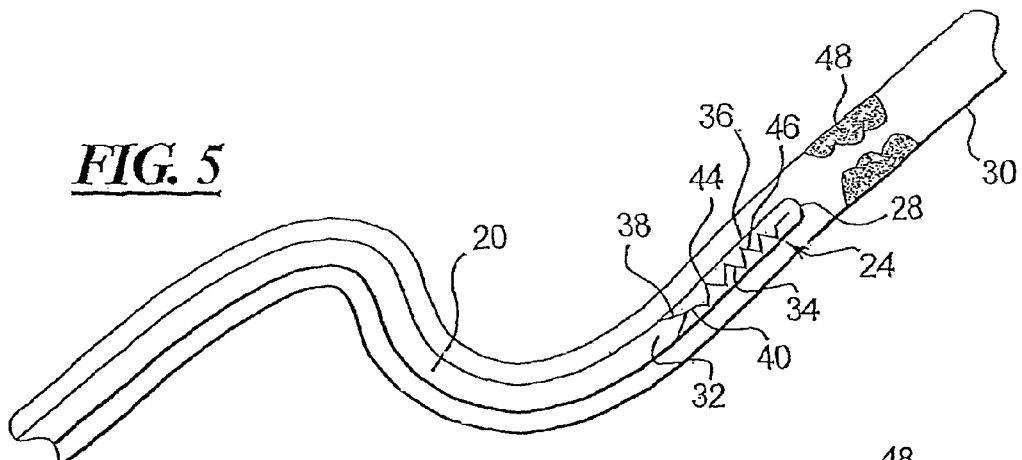
FIG. 5 is a perspective view of a guide wire approaching a lesion within a blood vessel.

As shown, the guide wire 20 includes a proximal region 22 opposite a distal region 24, with the proximal region including a proximal end 26 and the distal region 24 including a distal tip 28. As one of ordinary skill in the art will readily understand, the distal tip 28 is the tip of the guide wire 20 which navigates through a body lumen 30 as shown in FIGS. 5-7, while the proximal region 22 is the area handled by the physician or technician for pushing, turning, and otherwise manipulating the guide wire 20 as it navigates through the lumen 30.

The guide wire 20 includes a base or core wire 32 from which a shaping ribbon 34 extends at the distal tip 28. A sleeve 36 may extend over the shaping ribbon 34 and at least a portion of the core wire 32. The core wire 32 may terminate in a tapered end 38 and a flatten 40 from which the shaping ribbon 34 extends. In some embodiments, the shaping ribbon 34 is separate from the flatten 40 and attached thereto. In other embodiments the shaping ribbon 34 is unitary with the flatten 40 and the tapered end 38.

With respect to the materials from which the components can be manufactured, the core wire 32, as well as the shaping ribbon 34, can be manufactured from any suitable material including, but not limited to, metals, metal alloys, or any other suitable material. Some examples of suitable metals and metal alloys include stainless steel, such as 304V, 304L, and 316L stainless steel; alloys including nickel-titanium alloys such as linear elastic or superelastic (i.e., pseudoelastic) nitinol; nickel-chromium alloys; nickel-chromium-iron alloys; cobalt alloys; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% C a maximum 0.15% Mn, and a maximum 0.15% Si); HASTELLOY®, (an alloy of nickel with varying percentages of molybdenum, chromium, cobalt, iron, copper, manganese, titanium, zirconium, aluminum, carbon, and tungsten); MONEL® 400, (an alloy of nickel, copper, iron, manganese, carbon, silicon, and sulfur); INCONEL® Alloy 825, (a nickel-iron-chromium alloy with additions of copper, and molybdenum); or the like or other suitable materials. In some embodiments the core wire 32 and shaping ribbon 34 are made from different materials. In other embodiments, the core wire 32 and shaping ribbon 34 are made from the same material.

Figure 6:
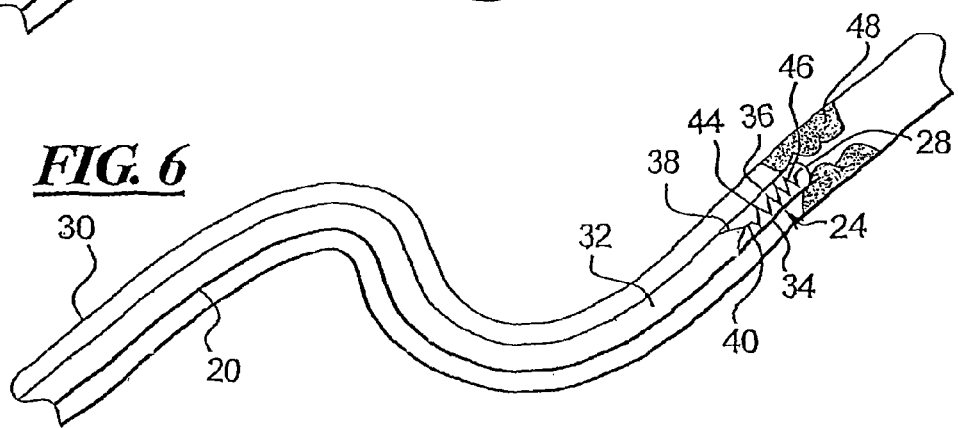
FIG. 6 is a perspective view similar to FIG. 5 but showing the guide wire engaging a lesion within the blood vessel and compressing.
Figure 7:
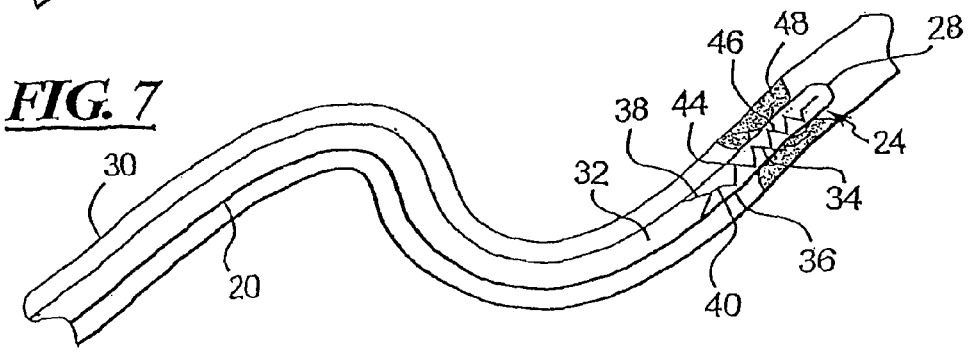
FIG. 7 is a perspective view of a guide wire advancing through the lesion of the blood vessel.
Figure 8:
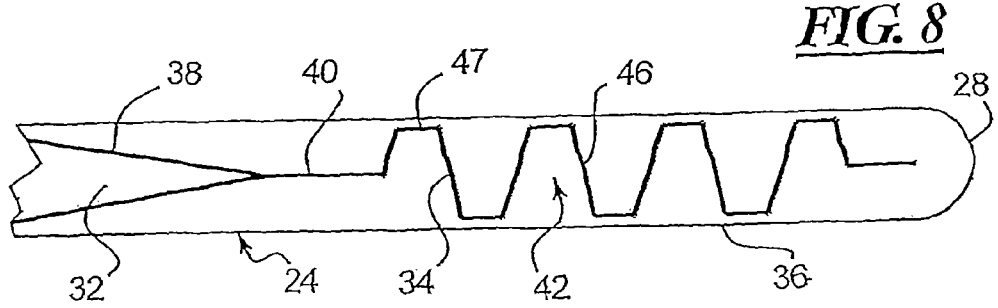
FIG. 8 is a longitudinal sectional view similar to FIG. 3, but showing an alternative embodiment.

As can be seen from any of FIGS. 3 and 5-7, the shaping ribbon 34 includes a plurality of corrugations 42 formed by bending the shaping ribbon 34 at pivot points 44 forming legs 46 therebetween. Accordingly, when a force is directed along the longitudinal axis a of the shaping ribbon 34, the shaping ribbon 34 tends to compress at pivot points 44 with legs 46 tending to become parallel to one another as shown in FIG. 6. It is to be understood that legs 46 need not come together at angled pivot points 44, but rather the legs 46 can be connected by flats 47 as shown in FIG. 8. With such an embodiment the shaping ribbon 34 would function in much the same fashion, as that of FIG. 3, compressing as it engages an occlusion and eventually expanding as it crosses through as more particularly described below.

Such constructions provide many benefits as the guide wire 20 is navigated through the body lumen 30. For example, as shown best in a comparison of FIGS. 5-7, as the guide wire 20 is navigated through the body lumen 30, the shape-ability of such a construction enables the distal tip 28 to bend and contort as the guide wire 20 navigates through the sometimes tortuous pathway of the body lumen 30. Upon reaching a lesion or other site of occlusion 48 wherein the body lumen 30, the shaping ribbon 34 may not immediately extend through the lesion 48. As such lesions or sites of occlusions 48 are typically of relatively hard material, significant force may need to be applied by the physician or technician at the proximal tip 26 to cause the guide wire 20 to extend through the lesion 48.

Accordingly, as can be seen best in FIG. 6, when initial contact is made with the lesion 48 and pressure is applied by the physician, the shaping ribbon 34 will tend to compress as shown therein. In so doing, the shaping ribbon 34 serves as a spring storing the energy being applied by the physician at the distal tip 28 within the legs 46 and pivot points 44 and/or flats 47 of the shaping ribbon 34. As additional force is applied by the physician at the distal region 24, eventually, the force applied by the physician and that stored within the shaping ribbon 34 will be sufficient to overcome the strength of the lesion 48, thus allowing the shaping ribbon 34 to expand and extend through the tissue of the lesion 48. This is shown best in FIG. 7.

Accordingly, it can be seen that not only does the shape of the ribbon 34 allow for the necessary shape-ability in the distal tip 28 to allow the guide wire 22 to effectively navigate through the body lumen 30, but the shape also enables sufficient force to be stored therein to facilitate the advancement of the guide wire 20 through a lesion or other site of occlusion. In addition, by manufacturing the shaping ribbon 34 from materials referenced herein, the shaping ribbon 34 is also to return to its uncompressed state shown in FIG. 5 even after advancing through the lesion 48.

Another benefit provided by such a guide wire is its track-ability. As one of ordinary skill in the art will readily understand, guide wires, catheters, and other elongate medical devices are often navigated through the body lumen 30 along significant distances to arrive at the site of occlusion, or other desired location. Such body lumens take many twists and turns along the way and it is important that any guide wire be able to follow that path or track. The construction of the present disclosure, with its ability to bend and contort, allows for such track-ability. The disclosure also allows for improved torque-ability as well, or in other words, the ability to be twisted or rotated with force, another key attribute of a guide wire.

Figure 3:
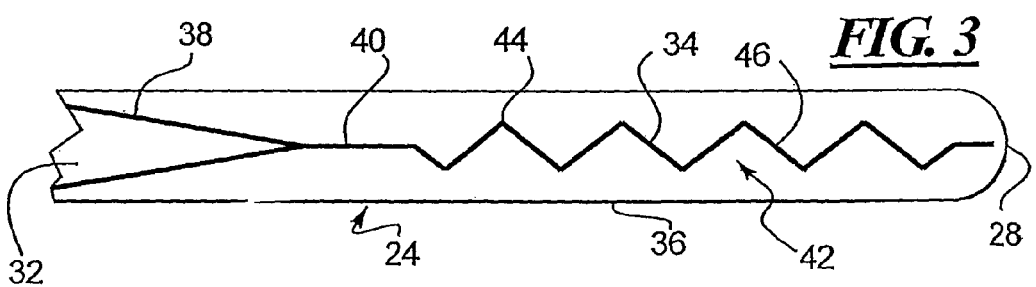
FIG. 3 is a longitudinal sectional view of FIG. 2, taken along line 3-3 of FIG. 2.
Figure 4:
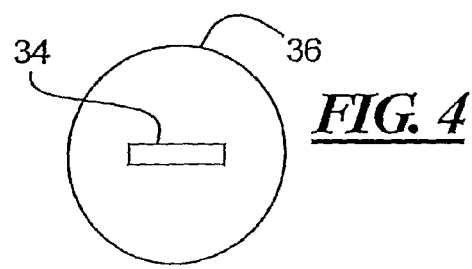
FIG. 4 is a lateral sectional view of FIG. 2, taken along line 4-4 of FIG. 2.

Referring now to FIGS. 3 and 4, sectional views of the shaping ribbon are provided. The lateral sectional view of FIG. 4 shows that the lateral cross-sectional shape of the shaping ribbon 34 can be provided in a rectangular configuration. However, it is to be understood that the teachings of the disclosure would allow for the shaping ribbon to be manufactured from any number of other lateral cross-sectional shapes including elliptical shapes, circular shapes, oval shapes, square shapes, triangular shapes, and any other polygonal shape.

In addition, the polymer sleeve need not be provided at all. In other words, in some embodiments the guide wire could consist of the core wire 32 and the shaping ribbon 34. However, the provision of the polymer sleeve 36 does allow for even greater cross-ability in the guide wire 20. In order to even further enhance the cross-ability or crossing performance of the guide wire 20, a coating (not shown) could be provided thereon which may be lubricious, hydrophilic, hydrophobic, a protective, a medicated, or other type of coating. Suitable materials for the coating are well known in the art and may include, but not limited to, silicon, polysulfones, polyfluorocarbons (such as TEFLON), polyolefins such as polyethylene, polypropylene, polyesters (including polyamides such as nylon), polyurethanes, polyarylene oxides, polyvinylpyrolidones, polyvinylalcohols, hydroxyl alkyl cellulosics, algins, saccharides, caprolactones, and the like and mixtures and combinations thereof. Suitable coating materials may be blended among themselves or with formulated amounts of water in soluble compounds (including some polymers) to yield a coating with suitable lubricity, bonding and solubility. Some other examples of such coatings and materials used to create such coatings can be found in U.S. Pat. Nos. 5,772,609, and 6,139,510, both of which are incorporated herein by reference.

In still further embodiments, the shaping ribbon 34 and/or the core wire 32 need not be surrounded by a polymer sleeve, but rather can be surrounded by a coil spring or the like (not shown). Such an embodiment would still have good shape-ability, cross-ability, and track-ability as long as its dimensions are kept uniform through its length.

Based on the foregoing, it can be seen that the teachings of the present disclosure provide an apparatus and method for constructing and navigating a guide wire through a body lumen. The guide wire includes a corrugated distal tip which improves the shape-ability, cross-ability, and track-ability of the medical device.

In addition, numerous characteristics and advantages of the invention covered by this document have been set forth in the forgoing description. It will be understood, however, that this disclosure is in many respects, only illustrative. Changes may be made in details, particularly in the matters of shape, size, and arrangement of parts without exceeding the scope of the invention. The invention scope is, of course, defined in the language in which the appended claims are expressed.

What is claimed is:

1. A crossing guide wire, comprising:
   a core wire having a proximal end and a distal end;
   a corrugated wire spring extending distally from the core wire distal end; and
   a sleeve positioned over the corrugated wire spring and at least a portion of the core wire, the sleeve having a distal tip;
   wherein the corrugated wire spring is configured to compress longitudinally and store energy applied at the distal tip by a force along a longitudinal axis thereof.

2. The crossing guide wire of claim 1, wherein the corrugated wire spring is manufactured from a nickel-chromium-iron-molybdenum-copper-titanium alloy.

3. The crossing guide wire of claim 1, wherein the spring is manufactured from stainless steel.

4. The crossing guide wire of claim 1, wherein the corrugated wire spring is formed by bending the wire at a plurality of pivot points to form a plurality of legs therebetween.

5. The crossing guide wire of claim 4, wherein the corrugated wire spring compresses at the plurality of pivot points such that the plurality of legs become parallel to one another.

6. The crossing guide wire of claim 1, wherein the corrugated wire spring returns to an uncompressed state when the force is removed.

7. The crossing guide wire of claim 1, wherein the distal end of the core wire includes a tapered end and a flatten.

8. The crossing guide wire of claim 7, wherein the corrugated wire spring is unitary with the flatten and the tapered end.

9. The crossing guide wire of claim 1, wherein the core wire and the corrugated wire spring are made from different materials.

10. The crossing guide wire of claim 1, wherein the core wire and the corrugated wire spring are made from the same material.

* * * * *